(12) United States Patent
Brady et al.

(10) Patent No.: US 9,169,284 B2
(45) Date of Patent: Oct. 27, 2015

(54) USE OF MICROFABRICATED DEVICES

(71) Applicant: HAMMERSMITH IMANET LIMITED, London (GB)

(72) Inventors: Frank Brady, London (GB); Sajinder Kaur Luthra, London (GB); James Millar Gillies, Lancashire (GB); Nicholas Toby Jeffrey, Caerphilly (GB)

(73) Assignee: Hammersmith Imanet Limited, London (GB)

( * ) Notice: Subject to any disclaimer, the term of this patent is extended or adjusted under 35 U.S.C. 154(b) by 0 days.

(21) Appl. No.: 14/253,049

(22) Filed: Apr. 15, 2014

(65) Prior Publication Data
US 2014/0316130 A1    Oct. 23, 2014

Related U.S. Application Data (63) Continuation of application No. 10/507,964, filed as application No. PCT/GB03/01097 on Mar. 14, 2003, now abandoned.

(30) Foreign Application Priority Data

Mar. 15, 2002 (GB) .................. 0206117.4

(51) Int. Cl.
*B01J 19/00* (2006.01)
*C07H 5/02* (2006.01)
*C07B 59/00* (2006.01)
*C07C 211/48* (2006.01)
*C07C 229/36* (2006.01)
*C07D 223/16* (2006.01)
*C07D 401/04* (2006.01)
*B01L 3/00* (2006.01)

(52) U.S. Cl.
CPC .............. *C07H 5/02* (2013.01); *B01J 19/0093* (2013.01); *C07B 59/00* (2013.01); *C07C 211/48* (2013.01); *C07C 229/36* (2013.01); *C07D 223/16* (2013.01); *C07D 401/04* (2013.01); *B01J 2219/00783* (2013.01); *B01J 2219/00889* (2013.01); *B01J 2219/00905* (2013.01); *B01J 2219/00952* (2013.01); *B01L 3/5027* (2013.01); *B01L 3/502715* (2013.01); *C07B 59/001* (2013.01); *C07B 59/002* (2013.01); *C07B 59/005* (2013.01)

(58) Field of Classification Search
CPC .............. B01J 19/0046; B01J 19/0093; B01J 2219/00659; B01J 2219/00722; B01J 19/00; B01J 19/2019; B01J 19/2219; B01J 19/00603
USPC .................................... 422/68.1, 50, 159, 129
See application file for complete search history.

(56) References Cited

U.S. PATENT DOCUMENTS 5,808,020 A * 9/1998 Ferrieri et al. ............... 536/18.5
6,010,607 A * 1/2000 Ramsey ........................ 204/435

* cited by examiner

*Primary Examiner* — Christine T Mui
(74) *Attorney, Agent, or Firm* — Parks Wood LLC (57) ABSTRACT

This invention relates to the miniaturization of radiosyntheses onto microfabricated devices, and in particular to use of microfabricated devices for radiosynthesis, isolation, and analysis of radiotracers for use in Positron Emission Tomography (PET).

20 Claims, 4 Drawing Sheets

USE OF MICROFABRICATED DEVICES

CROSS-REFERENCE TO RELATED APPLICATIONS

This application is continuation of pending U.S. application Ser. No. 10/507,964, filed Sep. 15, 2004, which in turn is a filing under 35 U.S.C. 371 of international application number PCT/GB2003/001097, filed Mar. 14, 2003, which claims priority to application number 0206117.4 filed Mar. 15, 2002, in Great Britain the entire disclosure of which is hereby incorporated by reference.

FIELD OF INVENTION

This invention relates to the miniaturisation of radiosyntheses onto microfabricated devices, and in particular to use of microfabricated devices for radiosynthesis, isolation, and analysis of radiotracers for use in Positron Emission Tomography (PET).

BACKGROUND OF THE INVENTION

The short half lives of the radioisotopes used for PET radiochemistry require that radiosyntheses are currently carried out rapidly and efficiently. Radiosyntheses and isolation of radiolabelled products are carried out using automated systems which are contained in large lead shielded "hot cells" to prevent radiation exposure to the operator. Such systems typically handle liquid volumes in the range 0.2 to 0.5 milliliters, though the number of radioactive atoms or molecules present is extremely small, typically $6.23 \times 10^{11}$ atoms or molecules. The current approach to automation of radiosyntheses is limited in flexibility and capacity and is also space consuming. There is also a need for automated radiosynthesis systems which are smaller, simpler, more flexible, multi-tasking, and with greater throughput capacity.

The radiosynthesis of radiotracers for PET involves several steps ranging from radioisotope production, incorporation of radioisotopes into suitable radiolabelling agents, radiolabelling of precursors, purification of radiolabelled products, and quality control analysis. Despite these many steps, the short half-lives of the radioisotopes used, require that the radiosynthesis is carried out rapidly and efficiently.

We now propose that performing radiochemistry on microfabricated devices will allow miniaturisation of automated radiosynthesis systems, or components thereof and hence may solve some of these problems. A major advantage of the proposed technology is that it will provide a generic system for performing radiochemistry with any isotope, for example, carbon-11 or fluorine-18. This approach may also allow simplification of automated synthesis systems, increased radiochemical yield and specific radioactivity of products because of shorter and more efficient reactions and more rapid isolation and analysis, and higher throughput because of the use of mass-produced disposable components.

Microreactors used for biochemical reactions have generally concentrated on developing continuous flow polymerase chain reactions (PCR) on a chip coupled with DNA sequencing using capilliary electrophoresis (CE), and microchip devices for performing enzyme assays. Until relatively recently, microfabrication research has concentrated on developing analytical microstructures rather than chemical synthesis microstructures. Reviews of methods for construction of microfabricated devices and their application inter alia in synthetic chemistry, may be found in DeWitt, (1999) "Microreactors for Chemical Synthesis", Current Opinion in Chemical Biology, 3:350-6; Haswell, Middleton et al (2001) "The Application of Microreactors to Synthetic Chemistry", Chemical Communications: 391-8; Haswell and Skelton (2000) "Chemical and Biochemical Microreactors", Trends in Analytical Chemistry 19(6), 389-395; and Jensen (2001) "Microreaction Engineering—Is Small Better?" Chemical Engineering Science, 56:293-303.

SUMMARY OF THE INVENTION

According to the present invention, there is provided the use of a microfabricated device for radiosynthesis, in particular, for radiosynthesis of a radiotracer suitable for use in PET, labelled with a positron emitting radionuclide such as $^{11}C$, $^{18}F$, or $^{124}I$, $^{13}N$, or $^{15}O$. In a preferred aspect, the radiotracer produced is labelled with $^{11}C$, $^{18}F$, or $^{124}I$, more preferably, $^{11}C$ or $^{18}F$. Examples of PET radiotracers which may be prepared by the claimed methods include 2-[$^{18}F$]fluorodeoxyglucose and L-6-[$^{18}F$]fluoro-DOPA. Further examples of PET radiotracers which may be prepared by the claimed methods include 3'-deoxy-3'-fluorothymidine (FLT), 2-(1,1-dicyanopropen-2-yl)-6-(2-fluoroethyl)-methylamino)-naphthalene (FDDNP), 5[$^{18}F$]fluorouracil, 5[$^{18}F$]fluorocytosine, and [$^{18}F$]-1-amino-3-fluorocyclobutane-1-carboxylic acid ([$^{18}F$]-FACBC).

The methods of the invention comprise one or more of the following steps performed on a microfabricated device:
(i) synthesis of a radiolabelling agent;
(ii) mixing and reaction of a radiolabelling agent with a precursor, suitably a radiotracer precursor to produce a radiolabelled product (suitably a radiotracer);
(iii) chemical modification of a radiolabelled product, suitably, to form a radiotracer;
(iv) analysis of a radiolabelled product, suitably, a radiotracer; and/or
(v) separation of a radiolabelled product, suitably a radiotracer, from one or more by-products.

According to a further aspect of the instant invention, the methods of the invention comprise one or more of the following steps performed on a microfabricated device:
(i) pre-treatment of a radioactive reagent or a precursor (suitably a radiotracer precursor);
(ii) synthesis of a radiolabelling agent;
(iii) mixing and reaction of a radiolabelling agent with a precursor, suitably a radiotracer precursor to produce a radiolabelled product (suitably a radiotracer);
(iv) chemical modification of a radiolabelled product, suitably, to form a radiotracer;
(v) analysis of a radiolabelled product, suitably, a radiotracer; and/or
(vi) separation of a radiolabelled product, suitably a radiotracer, from one or more by-products.

DETAILED DESCRIPTION OF THE PREFERRED EMBODIMENTS OF THE INVENTION

The term "radiotracer" as used herein includes carrier-added and no carrier-added radiolabelled compounds, and in particular includes radioligands (compounds radiolabelled at high specific activity).

The methods of the invention comprise one or more of the following steps performed on a microfabricated device:
(i) synthesis of a radiolabelling agent;
(v) mixing and reaction of a radiolabelling agent with a precursor, suitably a radiotracer precursor to produce a radiolabelled product (suitably a radiotracer);
(vi) chemical modification of a radiolabelled product, suitably, to form a radiotracer;
(iv) analysis of a radiolabelled product, suitably, a radiotracer; and/or
(v) separation of a radiolabelled product, suitably a radiotracer, from one or more by-products.

As a further step, the methods of the invention may also comprise pre-treatment of one or more radioactive reagents or a precursor used in the radiosynthesis. Examples of such pre-treatment include filtration, pre-concentration, isolation or activation of the reagent or precursor.

Therefore, according to a further aspect, the methods of the invention comprise one or more of the following steps performed on a microfabricated device:
(i) pre-treatment of a radioactive reagent or a precursor (suitably a radiotracer precursor);
(ii) synthesis of a radiolabelling agent;
(iii) mixing and reaction of a radiolabelling agent with a precursor, suitably a radiotracer precursor to produce a radiolabelled product (suitably a radiotracer);
(vii) chemical modification of a radiolabelled product, suitably, to form a radiotracer;
(v) analysis of a radiolabelled product, suitably, a radiotracer; and/or
(vi) separation of a radiolabelled product, suitably a radiotracer, from one or more by-products.

Typically, the chemistries used in radiosynthesis of radiolabelled products such as PET radiotracers include iodination, for example with iodine-124, methylation, for example using [$^{11}$C]iodomethane, and nucleophilic fluorinations, for example using [$^{18}$F]fluoride. Thus, [$^{11}$C]iodomethane may be used to form N-$^{11}$CH$_3$, O-$^{11}$CH$_3$, and S-$^{11}$CH$_3$ bonds, and fluorine-18 may be introduced into a variety of aliphatic and aromatic compounds via nucleophilic substitution.

The methods and apparatus of the invention are primarily intended for use with positron emitting radionuclides such as carbon-11 (half life 20.1 minutes), fluorine-18 (half life 110 minutes), and iodine-124 (half life 4.2 days). Other suitable radionuclides include iron-52 (half-life 8.3 hours), cobalt-55 (half-life 17.5 hours), copper-62 (half-life 9.7 minutes), bromine-75 (half-life 98.0 minutes), bromine-76 (half-life 16.1 hours), gallium-68, and technetium-94m (half-life 53 minutes). However, the anticipated increase in reaction rates that may be obtained using microfabricated devices may permit application to development of more complex radiochemistry with very short lived radioisotopes such as carbon-10, (half life 19.3 seconds) nitrogen-13 (half life 10.0 minutes), or oxygen-15 (half life 2.03 minutes). In addition to use with positron emitting radionuclides the devices described could also be applied to radiochemistry with gamma emitters such as technetium-99m, indium-111, gallium-67, iodine-123, iodine-125 and beta emitters such as carbon-14, tritium and phosphorus-32.

In more general terms, the PET radiotracers which may be prepared by the claimed methods include those synthesised by the use of radiolabelling agents well known to those skilled in the art, for example [$^{11}$C]methane, [$^{11}$C]carbon dioxide or [$^{11}$C]carbon monoxide. These include radiotracers synthesised by [$^{11}$C]alkylation or [$^{11}$C]fluoroalkylation of —NH, —OH and —SH groups in suitable precursors using [$^{11}$C]RX, wherein R is selected from methyl, ethyl, n-propyl, i-propyl, cyclopropyl, benzyl, cyclopentylmethyl, cyclohexylmethyl, and fluoro- or halo-analogues thereof; and X is selected from halo, mesylate, tosylate, triflate, nonaflate, nitrate, thiol, isocyanate, lithium and aldehyde. Examples of radiotracers thus prepared (using a radiolabelling agent in which R is methyl) are shown in Scheme 1.

Scheme 1.

[$^{11}$C]Flumazenil (I)

[$^{11}$C]Raclopride

L-[1-$^{11}$C]Methionine

A second group of radiolabelling agents used are those derived from Grignard reagents [$^{11}$C]R'MgX' (R' is selected from alkyl, cycloalkyl, alkenyl, and aromatic; and X' is halo. These include acid chlorides R'[$^{11}$C]COCl, acids R'[$^{11}$C]COOH, alcohols R'[$^{11}$C]CH$_2$OH, aldehydes R'[$^{11}$C]COH and ketones R'[$^{11}$C]COR' where R' is selected from methyl, ethyl, n-propyl, i-propyl, cyclopropyl, benzyl, cyclopentylmethyl, cyclohexylmethyl, and fluoro- or halo-analogues thereof. An example of a radiotracer prepared using derivatives of Grignard reagents is [carbonyl-$^{11}$C]-4-(2'-methoxy)phenyl-1-[2'-(N-2''-pyridinyl)cyclohexylamido]-ethylpiperazine.

A third group of radiolabelling agents used are derived mainly though not exclusively from [$^{11}$C]methane, include [$^{11}$C]CN$^-$ and [$^{11}$C]CCl$_4$. These are generally converted to bifunctional radiolabelling agents such as [$^{11}$C]phosgene, [$^{11}$C]urea and [$^{11}$C]cyanogen bromide for radiolabelling compounds of clinical interest. Examples of radiotracers prepared using some of these are shown in Scheme 2.

Scheme 2

S-[carbonyl-11C]CGP 12177

2-[$^{11}$C]Thymidine

Fluorine-18 is introduced into compounds of clinical interest for PET studies mainly by nucleophilic substitution reactions. Typically, [$^{18}$F]fluoride is prepared as an anhydrous potassium salt complex with the phase transfer catalyst Kryptofix 2.2.2. (trademark) or as a tetraalkylammonium salt or as a metal fluoride, in anhydrous non-protic solvents such as acetonitrile, DMSO or DMF by standard methods known to those skilled in the art. These solutions of [$^{18}$F]fluoride are used to carry out nucleophilic fluorinations by displacement of leaving groups such as halogens, mesylate, tosylate, triflate, nonaflate or sulphamate from a suitable precursor. Thus fluorine-18 may be introduced into a variety of aliphatic, aromatic, heterocyclic compounds and macromolecules via nucleophilic substitution on either intact molecules or on small radiolabelling agents which themselves may be subsequently used to radiolabel the compound of interest. For example compounds may be radiolabelled using [$^{18}$F]fluoroalkylations with [$^{18}$F]fluoromethyl-, [$^{18}$F]fluoroethyl- and [$^{18}$F]fluoropropyl-containing groups and others synthesised from [$^{18}$F]fluoride via nucleophilic displacement of suitable leaving groups, including halogens, mesylates, triflates, nonaflates or iodonium groups. Examples of radiotracers synthesised from [$^{18}$F]fluoride include 2-[$^{18}$F]FDG, and 6-[$^{18}$F]fluorodopa.

PET radiotracers may also radiolabelled with iodine-124, either by direct iodination using [$^{124}$I]iodide in the presence of a suitable oxidising agent such as chloramine-T or others known to those skilled in the art. Alternatively it may be first incorporated into a small molecule, usually aromatic and well known to those skilled in the art, which contains a second functional group allowing it to be chemically attached to the compound of clinical interest. Iodine-124 is particularly, but not exclusively, used for radiolabelling macromolecules such as peptides, proteins, antibodies and oligonucleotides.

According to a further aspect of the present invention, there is provided a microfabricated device adapted to carry out one or more of these steps, thus comprising one or more of:
(i) microfabricated mixing and reaction device;
(ii) microfabricated analysis device; and/or
(iii) microfabricated separation device.

Due to the nature of the radiolabelling agents and radiolabelled products, such microfabricated devices are typically provided with shielding to protect the operator from radioactive contamination. Such shielding suitably takes the form of a lead barrier or box around the device. Furthermore, the microfabricated devices according to the invention are suitably connected to or incorporate a means of radiochemical detection, for example a positron detector or HPLC system fitted with a radioactivity detector.

A microfabricated mixing and reaction element has been designed to incorporate multiple capillary channels, mixing chambers and is combined with heating elements. Flow through the device may be controlled using pressure, for example using micro-syringe pumps or electroosmotic flow. A second analytical element, a planar plastic or glass/silica microstructure etched with a single channel or multiple channels and incorporating an electrochemical detector and linked to a positron detector, may be used to analyse radiolabelled products. The device may be driven by pressure or by an electroosmotic flow. A third microfabricated device etched with multiple separation channels may be used to separate and isolate radiolabelled compounds. The methodology developed using these devices for radiolabelling, isolation and analysis of products may be combined onto a single microfabricated device incorporating features of the preparative analytical and separation elements described.

In such devices, predetermined networks of microchannels or capillaries, typically 10-300 μm, more typically 50-300 μm in diameter, are etched or otherwise machined on the surface of a substrate, suitably made of glass or silicon. Alternatively, the microchannels may be created using polymers (for example PEEK plastic, polydimethylsiloxane, SU8 (an epoxy based photoresist), epoxy resin, or polymethylmethacrylate) which may be poured over a master (usually glass), allowed to cure and then peeled off, or are fabricated by injection moulding, hot embossing, casting, lithography, or machining.

These channels may be sealed through bonding of a cover plate, suitably made from a metal (for example, gold or silver) or, more commonly, glass, creating a contained network capable of manipulating picoliter volumes of liquid or gas. The sealing method used depends on the materials selected and may be selected from thermal bonding (for glass chips), anodic bonding (for silicon chips), and for polymer chips the sealing method may be selected from clamping, gluing, application of heat and pressure, and natural adhesion. Nanoliter and picoliter volumes may be used for analytical aspects but the devices can handle flows of up to hundreds of microliters per minute. This could be increased further, for example, by stacking multiple devices. These devices are designed to be used either with micro syringe pumps (available from Kloehen Limited, Las Vegas, USA) or under electroosmotic flow using fused silica capillaries for interfacing with reagents and analytical systems (such as ultraviolet (UV), capillary electrophoresis (CE), capillary electrochromatography (CEC), electrochemical, refractive index, and radioactivity detectors).

Radioanalytical procedures have not previously been carried out on a microfabricated device. A major hurdle in achieving this has been the difficulty of interfacing the microfabricated device to external reagent supplies and suitable radioactivity detectors. Use of an on-line miniaturised positron detector, (for example as described in WO 99/67656 or in Gillies et al, J. Label. Compds. Radiopharm., 42, S886-S888 (1999)) will allow interface with the microfabricated device via the capillary to a capillary electrophoresis (CE) or capillary electrochromatography (CEC) system. When used with large (eg >1 mCi) amounts of radioactivity the device may be linked to a conventional HPLC system fitted with radioactivity and UV or electrochemical detectors.

Figure 1:
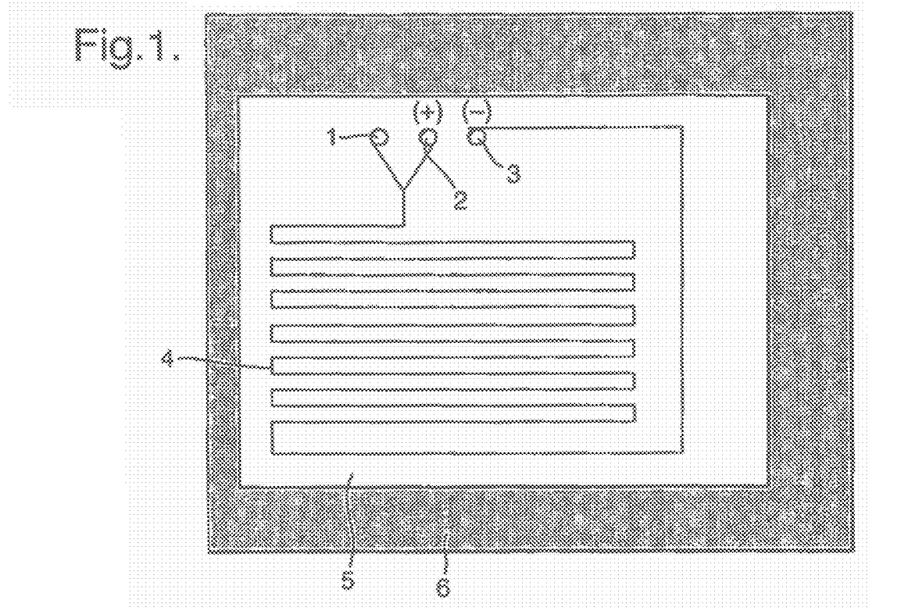
FIG. 1 is a diagrammatic representation in plan of an individual microchannel element of the microfabricated apparatus for performing radiosynthesis and synthesis of radiolabelled products for use as radiotracers.
Figure 2:
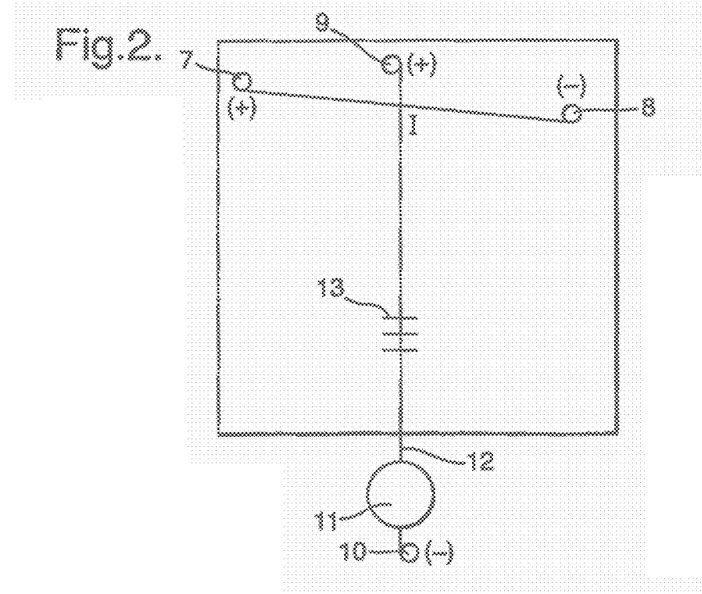
FIG. 2 is a diagrammatic plan view of a microchannel analytical element of a microfabricated device incorporating an electrochemical detector and connected to a positron detector via a fused silica capillary or suitable inert capillary bore plastic tubing (for example, PEEK or TEFLON)
Figure 3:
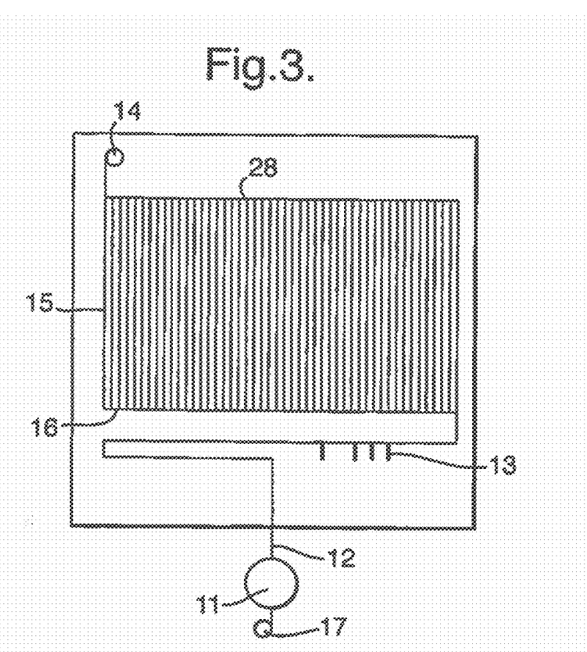
FIG. 3 is a diagrammatic plan view of the microchannel separation element of a microfabricated device incorporating an electrochemical detector and connected to a positron detector via a fused silica capillary or suitable inert capillary bore plastic tubing (for example, PEEK or TEFLON) for carrying out chromatographic separation of radioactive and non-radioactive reaction products and precursors.
Figure 4:
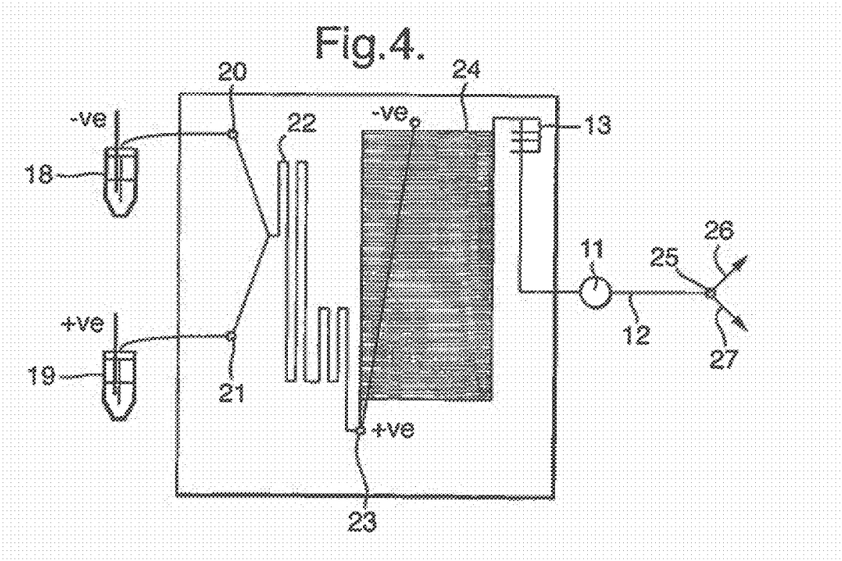
FIG. 4 is a diagrammatic view of a microfabricated device capable of carrying out all the functions of the elements shown in FIGS. 1-3, namely mixing and reaction, separation and analysis, on a single chip. This is shown linked to inlet reservoirs for reactants and to a positron detector and a manifold for collecting products or diverting eluent to waste, via a fused silica capillary or suitable inert capillary bore plastic tubing (for example, PEEK or TEFLON).

The invention will be further illustrated, by way of example, with reference to the following Drawings:

FIG. 1 is a diagrammatic representation in plan of an individual microchannel element of the microfabricated apparatus for performing radiosynthesis and synthesis of radiolabelled products for use as radiotracers;

FIG. 2 is a diagrammatic plan view of a microchannel analytical element of a microfabricated device incorporating an electrochemical detector and connected to a positron detector via a fused silica capillary or suitable inert capillary bore plastic tubing (for example, PEEK or TEFLON);

FIG. 3 is a diagrammatic plan view of the microchannel separation element of a microfabricated device incorporating an electrochemical detector and connected to a positron detector via a fused silica capillary or suitable inert capillary bore plastic tubing (for example, PEEK or TEFLON) for carrying out chromatographic separation of radioactive and non-radioactive reaction products and precursors;

FIG. 4 is a diagrammatic view of a microfabricated device capable of carrying out all the functions of the elements shown in FIGS. 1-3, namely mixing and reaction, separation and analysis, on a single chip. This is shown linked to inlet reservoirs for reactants and to a positron detector and a manifold for collecting products or diverting eluent to waste, via a fused silica capillary or suitable inert capillary bore plastic tubing (for example, PEEK or TEFLON).

Figure 5:
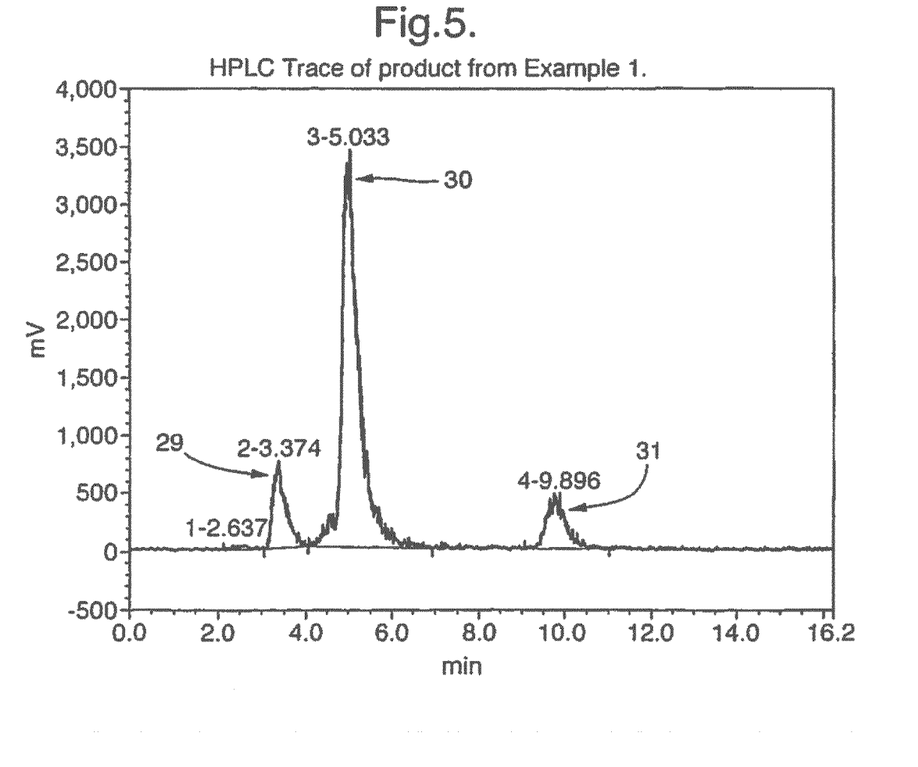
FIG. 5 is an HPLC trace of the product from Example 1.

FIG. 5 is an HPLC trace of the product from Example 1.

Figure 6:
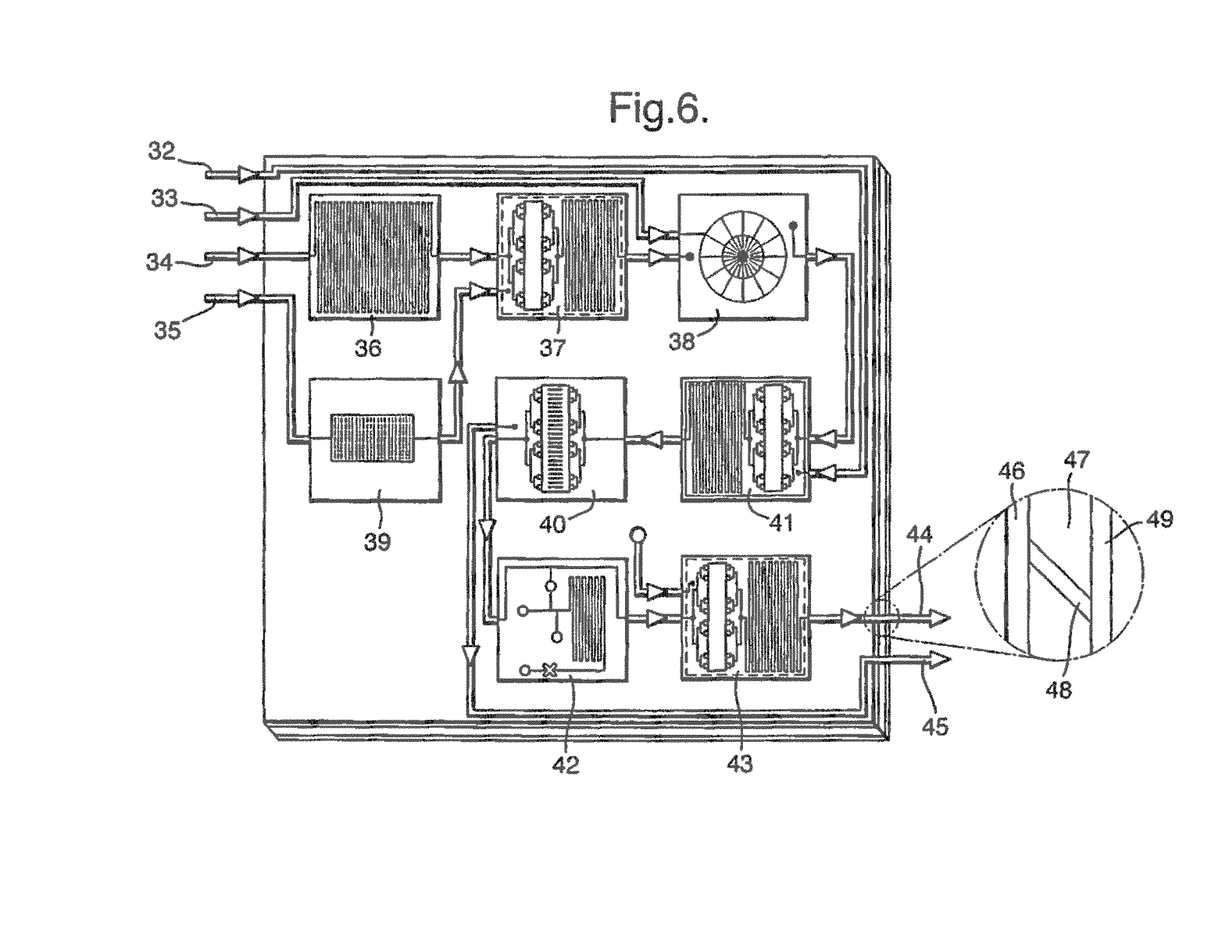
FIG. 6 is a diagrammatic plan view of a microfabricated total radiotracer synthesis system.

FIG. 6 is a diagrammatic plan view of a microfabricated total radiotracer synthesis system.

Referring to FIG. 1, the mixing/heating or reaction chip (5) is approximately 1 cm square and comprises glass, plastic, silica, metal, or a composite of any combination of these, microfabricated to provide inlet ports (1) and (2) for the introduction of radioactive and non-radioactive reactants in the form of gases, liquids or solutions or suspensions in suitable solvents and an outlet port (3) for the collection of the reaction mixture or components thereof. A third inlet port (not shown) may also be incorporated at some point along the microchannel to allow introduction of a third reagent, for example, for use in a deprotection step. These ports are linked to a system of microchannels which have been microfabricated onto the structure and which introduce the reactants into mixing channels (4) designed to provide rapid and efficient mixing and hence leading to rapid and efficient reaction and incorporation of radioisotopes into compounds of interest for use as radiopharmaceuticals. Reactants may be introduced onto the device using either microsyringe pumps or in certain cases using electroosmotic flow. The device may be heated, if required, by attachment of a suitable heating element (6). This device may be used alone or as a component of an automated radiosynthesis system to replace conventional glass, or other material such as plastic or glassy carbon, reaction pots currently in use, to simplify the automated system.

The reaction chip shown in FIG. 1 may be connected in series to, or stacked with, the device shown in FIG. 2, referred to as the analytical chip which is approximately 1 cm by 3 cm. This has an inlet port (7) and an outlet port (8) for respectively introducing and collecting reaction mixtures, or components thereof, into or out of the microchannel microfabricated onto the device. Two other ports (9) and (10) act as inlet and outlet respectively for a suitable electrolyte buffer solution. Application of a voltage to the device allows components of the reaction mixture or component thereof, to separate based on the principles of capillary electrophoresis. An electrochemical detector (13) consisting of, for example, platinum electrodes may be incorporated onto the device in such a position that it is in contact with the flowing reaction mixture or component thereof and is used to detect stable compounds in the solution. The outlet port (10) is connected to a suitable positron detector (11) via a fused silica capillary (12) or suitable inert capillary bore plastic tubing (for example, PEEK or TEFLON) for monitoring radioactive compounds. The device shown in FIG. 2 may be used as a component of an automated synthesis system, to simplify the system for producing radiolabelled compounds for use as radiopharmaceuticals, for analysing reaction mixtures of radiolabelled compounds or as a diagnostic device for checking the progress of a radiosynthetic procedure. It may be combined with the device in FIG. 1 (mixing, heating chip) to carry out a radiosynthesis and analyse the products of this.

A separation device is shown in FIG. 3, which is also approximately 1 cm by 3 cm. This is microfabricated to consist of an inlet port (14) leading to a manifold (28) which separates injected reaction mixtures into a series of parallel separation channels (15). Application of a high voltage across the device allows components of the reaction mixture to be separated by capillary electrophoresis. The outflow from all the channels is collected on an incorporated collection manifold (16). The collected eluate may then be passed through an incorporated mixing chamber (not shown) and thence to an incorporated electrochemical detector (13) and passed via outlet (17) through a fused silica capillary (12) or suitable inert capillary bore plastic tubing (for example, PEEK or TEFLON) to a positron detector (11). After passing the positron detector fractions of the sample may be collected or passed onto the analytical device shown in FIG. 2. The device shown in FIG. 3 may be used as a component of an automated synthesis system for producing separating and analysing radiolabelled compounds for use as radiopharmaceuticals.

FIG. 4 illustrates diagrammatically how all the features of the devices shown in FIGS. 1-3 are incorporated onto a single device. Reactants are introduced from reservoirs or sources (18 and 19) via fused silica capillaries or suitable inert capillary bore plastic tubing (for example, PEEK or TEFLON) through inlet ports (20, 21) microfabricated onto the device using either microsyringes (not shown) or capillary electrophoresis. The reaction mixture is then passed through a series of microchannels (22) where reaction occurs. The reaction mixture is then passed via an inlet (23) through an incorporated CE separation module (24) consisting of a series of parallel microchannels as described in FIG. 3. The eluate from the separation module is then passed through an incorporated electrochemical detector (13) and thence via an outlet (25) through a positron detector (11) followed by collection of desired product(s) (positive) (26) or elution to waste (negative) (27). This device is thus capable of carrying out all the steps in a radiosynthesis; mixing and reaction, separation, isolation and analysis of product(s). The invention described may be used as a component of an automated synthesis system for producing, separating and analysing radiolabelled compounds for use as radiopharmaceuticals.

FIG. 6 illustrates a microfabricated total radiotracer synthesis system which is around 76 mm square. All aspects of radiotracer production may be achieved in continuous flow on a single integrated microfabricated device. Thus, reagents and precursors are introduced through inlets (32), (33), (34), and (35) and may be subject to a pre-concentration module (36), or filtration module (39). Synthesis of a radiolabelling agent occurs (37) before mixing and reaction of the radiolabelling agent with a precursor to produce a radiolabelled product (38). Chemical modification of the radiolabelled product (e.g. deprotection) occurs (41) before purification (40), analysis (42), and formulation (43). Final product exits through outlet (44) and waste by-products through outlet (45). A small cross-section of the device shows construction from two glass plates (46) and (49), the polymer substrate (47) containing a microchannel through which the product flows (48).

The microfabricated devices described are designed to handle liquid or gas flow volumes of 10 nanoliters to 1 milliliter per minute however flow capacity may be increased by using stacked or parallel arrays of devices.

The invention will be further illustrated with reference to the following non-limiting examples:

EXAMPLES

Preparation of a Microfabricated Device Suitable for Radiosynthesis

76 mm Low Reflective Chrome (Cr1000), print grade sensitised, soda lime glass substrates of thickness 0.06 inches were purchased from Nanofilm (Westlake Village, Canada).

Microfabricated device design was done on a PC running AutoCad LT for Windows 95. Masks made using a direct write lithography system (prototype DWLII, Heidelberg Instruments) were used to shadow cast substrates. Wet etching used an aqueous solution 5% (7:1 $NH_4F:HF$), 9.25% HCl effecting etch rates of 0.2 µm $min^{-1}$, all channels were etched to 30 µm. Prior to bonding the pre-drilled cover plate (microscope slide) and etched substrate were sonicated in DMF, acetone and methanol (2 minutes each) and immersed in concentrated sulphuric acid (2 hours). Further washing with ultra pure water and drying under a flow of nitrogen, preceded loading of the furnace (Thermicon P, Heraeus instruments). Thermal bonding used a 12 hour ramped temperature programme with a maximum temperature of 600° C.

The following Examples demonstrate the principle that microfabricated devices may be used to carry out radiosynthesis.

Example 1

Radiolabelling of 2-[$^{18}$F]fluorodeoxyglucose (FDG) using [$^{18}$F]fluoride

R = triflate;
nonaflate

2-[$^{18}$F]FDG

Azeotropic drying of [$^{18}$F]fluoride was achieved using the following method. A glass drying-vessel was preloaded with Kryptofix[2.2.2.] (4 mg) and $K_2CO_3$ (4.6 mg) dissolved in 200 µl $H_2O$ and 800 µl acetonitrile. Into this vessel the aqueous [$^{18}$F]fluoride (circa 1 ml) was added and the vessel heated to 120° C. with an over flow of nitrogen gas (circa 2 ml $min^{-1}$). After 10 minutes of heating 1 ml of acetonitrile was added. Further 2 additions of 1 ml acetonitrile measures followed at 10 minute intervals until the fluoride was completely dry. Then with stirring at 80° C. (circa 2 min) the fluoride/Kryptofix[2.2.2.] residue was reconstituted in 1 ml acetonitrile (circa 26% efficient).

For 'on-chip' radiolabelling the dried $K^+/K$ 2.2.2/[$^{18}$F] fluoride in acetonitrile was infused (using precision syringe drives) into one of the two chip inlets while tetra-acetylmannose triflate (FDG precursor) solution (10 mg in 500 µl acetonitrile) was infused, at an equal rate, into the other. The total flow rate was varied between 5-100 µl $min^{-1}$ and the reaction was carried out at 75° C. to give 2-[$^{18}$F]fluorinated tetraacetylated deoxyglucose. Product mixture collected from the chip outlet was analysed by HPLC ($NH_3$ Nucleosil column 10µ 250×4.6 mm), flow rate 2 ml $min^{-1}$, mobile phase: 80% acetonitrile, 20% water. The product, unhydrolised FDG eluted at circa 2 minutes with no other radiochemical fraction evident. Radiochemical yield was 20-49%, n>10.

The acetyl protecting groups may be subsequently removed by acid or base hydrolysis by addition of an aqueous solution of hydrochloric acid or sodium hydroxide respectively. Thus, for example, by operating two microfabricated devices in series to extend the fluorination step to the deprotection step. 2-[$^{18}$F]fluorinated tetraacetylated deoxyglucose, prepared as described above, was fed into one port of a second identical device and aqueous sodium hydroxide was fed into a second port of the device. The solutions were mixed at room temperature to give 2-[$^{18}$F]fluoro-2-deoxy-D-glucose in 24% radiochemical yield. This was a continuous flow process, the residence time of the fluid on the combined device network being less than 1 minute.

An HPLC trace of the resulting product is shown in FIG. 5 in which peak (29) is 2-[$^{18}$F]fluorinated tetraacetylated deoxyglucose, peak (30) is [$^{18}$F]fluoride, and peak (31) is 2-[$^{18}$F]fluoro-2-deoxy-D-glucose.

Example 2

[$^{11}$C]Methylation of N-methylanaline

$\downarrow LiAlH_4$

Iodomethane in acetone and a solution of N-methylaniline containing sodium hydroxide in acetone at room temperature were introduced via fused silica capillaries onto the microfabricated mixing device. The eluate from the device was analysed by HPLC and shown to contain N,N'-dimethylaniline. [$^{11}$C]Iodomethane is used in the same way, with heating of the device, to produce N,N'-[$^{11}$C]dimethylaniline. Alternatively, [$^{11}$C]methyltriflate or nonaflate are used to produce the same compound without heating the device.

Example 3

Synthesis of L-3-[$^{124}$I]-iodotyrosine iodotyrosine

Aqueous solutions (containing 0.1 M KH$_2$PO$_4$) of iodide, chloramine-T and L-tyrosine were introduced onto a microfabricated device containing a mixing chamber (described in ref Gillies et a/above) via fused silica capillaries using Kloher micro syringe pumps under computer control at a flow rate of 50 μl per minute. The eluate from the device was analysed by reverse phase HPLC and shown to contain iodotyrosine which was isolated in pure form and its identity confirmed by mass spectrometry. The same procedure is used with iodine-124 to produce L-3-[$^{124}$I]iodotyrosine.

Example 4

N-[$^{11}$C]methylation of R(+)-7-chloro-8-hydroxy-3-[$^{11}$C]methyl-1-phenyl-2,3,4,5-tetrahydro-1H-3-benzazepine

[$^{11}$C]Methyl iodide in acetone was infused into one microchip inlet while precursor (1 mg) solution in acetone containing triethyl ether (2 μl) was infused, at an equal rate, into the remaining inlet. The conversion was effected at room temperature and flow rates of 10 to 100 μl min$^{-1}$, using methods analogous to those described in Example 2, giving the product in under 1 minute and in 5 to 19% radiochemical yield (n=5). Characterisation of the product was provided by mass spectrometry and nmr.

Example 5

N-[$^{11}$C]methylation of 2-pyridin-4-yl-quinoline-8-carboxylic acid (2-methylamino-ethyl)-amide This conversion was affected at room temperature at flow rates 10-100 μl min⁻¹, using methods analogues to those described in Example 2. Reaction times were less than one minute and radiochemical yields averaged 10% (n=2). Product was characterized by referenced HPLC.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. Use of a microfabricated device having 10 to 300 μm diameter microchannels or capillaries for continuous flow radiosynthesis and isolation of a radiotracer suitable for use in PET, wherein said radiosynthesis and isolation is performed at a flow rate of 10 nanoliters to 1 milliliter per minute.

2. Use according to claim 1 wherein the radiotracer produced is labelled with $^{11}C$, $^{18}F$, or $^{124}I$.

3. Use according to claim 1 wherein the radiotracer is 2-[$^{18}F$]fluorodeoxyglucose or L-6-[$^{18}F$]fluoro-DOPA.

4. Use according to claim 1, which comprises one or more of the steps (i) to (vi) performed on a microfabricated device:
    (i) pre-treatment of a radioactive reagent or a precursor;
    (ii) synthesis of a radiolabelling agent;
    (iii) mixing and reaction of a radiolabelling agent with a precursor to produce a radiolabelled product;
    (iv) chemical modification of a radiolabelled product;
    (v) analysis of a radiolabelled product; and/or
    (vi) separation of a radiolabelled product, from one or more by-products.

5. Use according to claim 4 wherein the radiolabelled product produced is a radiotracer such as 2-[$^{18}F$]fluorodeoxyglucose or L-6-[$^{18}F$]fluoro-DOPA.

6. Use according to claim 4 wherein the radiolabelling agent is selected from: [$^{11}C$]methane;
    [$^{11}C$]carbon dioxide;
    [$^{11}C$]carbon monoxide;
    [$^{11}C$]RX, wherein R is selected from methyl, ethyl, n-propyl, i-propyl, cyclopropyl, benzyl, cyclopentylmethyl, cyclohexylmethyl, and fluoro- or halo-analogues thereof; and X is selected from halo, mesylate, tosylate, triflate, nonaflate, nitrate, thiol, isocyanate, lithium and aldehyde;
    R'[$^{11}C$]COCl, R'[$^{11}C$]COOH, R'[$^{11}C$]CH$_2$OH, R'[$^{11}C$]COH, or
    R'[$^{11}C$]COR' where R' is selected from methyl, ethyl, n-propyl, i-propyl, cyclopropyl, benzyl, cyclopentylmethyl, cyclohexylmethyl, and fluoro- or halo-analogues thereof;
    [$^{11}C$]CN⁻;
    [$^{11}C$]CCl$_4$;
    [$^{11}C$]phosgene;
    [$^{11}C$]urea;
    [$^{11}C$]cyanogen bromide;
    [$^{18}F$]fluoride; and
    [$^{124}I$]iodide.

7. A microfabricated device adapted to carry out one or more of the steps in claim 5 comprising one or more of:
    (i) microfabricated mixing and reaction device;
    (ii) microfabricated analysis device; and/or
    (iii) microfabricated separation device.

8. The microfabricated device according to claim 7, wherein one or more of the (i) microfabricated mixing and reaction device, (ii) microfabricated analysis device, and (iii) microfabricated separation device comprise 10 to 300 μm diameter microchannels or capillaries.

9. The microfabricated device according to claim 7 wherein all of the devices (i)-(iii) are on a single chip.

10. Use according to claim 1 wherein the microchannels or capillaries are created onto a chip substrate by etching, machining, injection molding, hot embossing, casting, lithography, or are created from polymers that are poured on a master, cured and peeled.

11. Use according to claim 1, wherein a radiolabelling agent is produced in a process having a fluid residence time on the microfabricated device of less than one minute.

12. Use of a microfabricated device for continuous flow radiosynthesis of a radiotracer suitable for use in PET wherein said device comprises a chip substrate having a network of 10 to 300 μm diameter microchannels or capillaries, and is adapted to carry out the steps of radiolabelling, isolation, and analysis of radiolabelled compounds, and wherein said device is adapted to perform the radiolabelling and isolation steps at a flow rate of 10 nanoliters to 1 milliliter per minute.

13. Use according to claim 12 wherein the network of microchannels or capillaries are created on the chip substrate by etching, machining, injection molding, hot embossing, casting, or lithography, or are created from polymers that are poured on a master, cured and peeled.

14. Use according to claim 12, wherein the microchannels or capillaries are 10-300 μm in diameter.

15. Use of a stacked or parallel array of microfabricated devices for continuous flow radiosynthesis and isolation of a radiotracer suitable for use in PET, wherein said microfabricated devices have a network of 10 to 300 μm diameter microchannels or capillaries and said radiosyntheis and isolation is performed at a flow rate of 10 nanoliters to 1 milliliter per minute.

16. Use according to claim 15 which comprises one or more of the steps (i) to (vi) performed on a stacked or parallel array of microfabricated devices:
    (i) pre-treatment of a radioactive reagent or a precursor;
    (ii) synthesis of a radiolabelling agent;
    (iii) mixing and reaction of a radiolabelling agent with a precursor to produce a radiolabelled product;
    (iv) chemical modification of a radiolabelled product;
    (v) analysis of a radiolabelled product; and/or
    (vi) separation of a radiolabelled product, from one or more by-product.

17. A stacked or parallel array of microfabricated devices adapted to carry out one or more of the steps in claim 16 comprising one or more of:
    (i) microfabricated mixing and reaction device;
    (ii) microfabricated analysis device; and/or
    (iii) microfabricated separation device.

18. Use according to claim 1, wherein said microfabricated device comprises a capillary electrophoresis separation module consisting of a series of parallel 10 to 300 μm diameter microchannels, and an outlet passing through a positron detector.

19. Use according to claim 12, wherein said microfabricated device comprises a capillary electrophoresis separation module consisting of a series of parallel 10 to 300 μm diameter microchannels, and an outlet passing through a positron detector.

20. Use according to claim 15, wherein said array of microfabricated devices comprises a capillary electrophoresis separation module consisting of a series of parallel 10 to 300 μm diameter microchannels, and an outlet passing through a positron detector.

* * * * *